United States Patent [19]

Bartek et al.

[11] Patent Number: 5,198,580
[45] Date of Patent: Mar. 30, 1993

[54] PROCESS FOR OXIDATION OF PROPANE

[75] Inventors: Joseph P. Bartek, Highland Heights; Ann M. Ebner, Lyndhurst; James R. Brazdil, Mayfield Village, all of Ohio

[73] Assignee: The Standard Oil Company, Cleveland, Ohio

[21] Appl. No.: 793,910

[22] Filed: Nov. 18, 1991

[51] Int. Cl.$^5$ .............................................. C07C 51/16
[52] U.S. Cl. ..................... 562/542; 562/549
[58] Field of Search .................. 562/549, 542

[56] References Cited

U.S. PATENT DOCUMENTS 4,111,832  9/1978  Rohbock et al. ............... 562/549
4,250,346  2/1981  Young et al. .................. 562/549

FOREIGN PATENT DOCUMENTS 0117146  2/1984  European Pat. Off. .

Primary Examiner—José G. Dees
Assistant Examiner—Joseph M. Conrad
Attorney, Agent, or Firm—Charles S. Lynch; Michael F. Esposito; Larry W. Evans

[57] ABSTRACT

Disclosed is a process for the partial oxidation of propane to yield acrylic acid, propylene, acrolein and acetic acid by contacting propane in admixture with a molecular oxygen-containing gas in a reaction zone with an oxidic solid catalyst that 1) contains the components and proportions represented by the empirical formula $$Bi_bMo_cV_vA_aD_dE_eO_x$$

wherein
A is one or more of K, Na, Li, Cs and Tl,
D is one or more of Fe, Ni, Co, Zn, Ce and La,
E is one or more of W, Nb, Sb, Sn, P, Cu, Pb, B, Mg, Ca and Sr,
a, d and e are each zero-10
b is 0.1-10
c is 0.1-20
v is 0.1-10
c:b is from 2:1 to 30:1
v:b is from 1.5:1 to 8:1
and 2) is made by performing a bismuth molybdate containing composition having at least 0.67 atoms of Mo per atom of Bi, before combining with any vanadium compound.

2 Claims, No Drawings

PROCESS FOR OXIDATION OF PROPANE

The present invention relates to a method for the partial oxidation of propane to yield acrylic acid, propylene, acrolein and acetic acid.

U.S. Pat. No. 4,524,236 discloses catalysts for oxydehydrogenation of ethane to ethylene containing Mo, V, Nb, Sb and X, where X is one or more of Li, Sc, Na, Be, Mg, Ca, Sr, Ba, Ti, Zr, Hf, Y, Ta, Cr, Fe, Co, Ni, Ce, La, Zn, Cd, Hg, Al, Tl, Pb, As, Bi, Te, U and W, all as oxides. The X elements, including Bi, are added as soluble or insoluble compounds, preferably to the second solution containing Nb and Sb. That solution would be added to the vanadium source before adding a third solution containing ammonium molybdate. These catalysts are said to be unsuitable for the oxydehydrogenation of propane and butane because such catalysts "medaminantly burn these gases to carbon dioxide and other oxidized carbonaceous products".

Similar catalysts are disclosed for the same reaction in U.S. Pat. No. 4,250,346, the parent of U.S. Pat. No. 4,524,236, although Sb and Nb are optional in the earlier patent U.S. Pat. No. 4,260,822 discloses that catalysts of the formula $Mo_{(9-24)}Sb_{(0.25-2)}P_{(0.5-2)}$ in combination with oxygen can be used to oxidize propane to acrylic acid, acrolein, $CO_2$, CO and acetone. The results obtained with this catalyst when oxidizing propane are poor, with a low yield of acrylic acid and apparently none of the expected acrolein. See Example 3.

British patent specification 1,340,891 discloses using catalysts containing oxygen and at least two elements in various reactions of propane with oxygen. This reference contemplates that the oxidation of propane will yield one of several alternative products; (a) propylene or (b) acrolein or (c) acrylic acid. It is stated that the product obtained depends on the reaction conditions and the catalyst used. It also notes that "It is possible in some circumstances to obtain a mixture containing two or more desired products." The nature of the circumstances is unclear.

Particular catalysts are suggested for reactions (a) and (b); no particular catalysts are suggested for reaction (c). In any event, the only catalysts suggested for oxidation of propane are in examples 24–32 for conversion of the propane feed to propylene. No catalyst containing oxygen and Bi, V and Mo is suggested for any reaction whatsoever.

Indirect processes for conversion of propane to acrylic acid, i.e., those where acrylic acid is not made in the propane conversion step, have been disclosed, but most separate propylene from the first stage, dehydrogenation effluent. Khoobiar and Porcelli of Halcon SD have disclosed a propane conversion process where the dehydrogenation products are passed to the second, propylene oxidation stage without separation (European Pat. App. 0 117 145,9/84). They found that the propylene in a dilute feed, also containing nearly as much propane or hydrogen, was converted preferentially to acrolein and acrylic acid. Overall selectivity from propane to acrylic acid is the product of the selectivities of all stages, since no acrylic acid is made directly from propane. Such processes need a high temperature endothermic reactor, with an outlet temperature of at least 550° C. as the first state. Excess steam diluent as much as 2/1 $H_2O/C_3H_8$, must also be heated to the reactor inlet temperature about 600° C.

It is an object of the present invention to provide an improved process for the partial oxidation of propane with molecular oxygen to acrylic acid and other partial oxidation products before mentioned.

Other objects as well as aspects, features and advantages of the present invention will become apparent from a study of the present specification, including the claims and the specific examples.

According to the present invention there is provided a process for the partial oxidation of propane to yield acrylic acid, propylene, acrolein and acetic acid by contacting propane in admixture with a molecular oxygen-containing gas in a reaction zone with an oxidic solid catalyst that 1) contains the components and proportions represented by the empirical formula

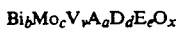
$$Bi_bMo_cV_vA_aD_dE_eO_x$$

wherein
  A is one or more of K, Na, Li, Cs and Tl,
  D is one or more of Fe, Ni, Co, Zn, Ce, and La,
  E is one or more of W, Nb, Sb, Sn, P, Cu, Pb, B, Mg, Ca and Sr,
  a, d and e are each zero-10
  b is 0.1–10
  c is 0.1–20
  v is 0.1–10
  c:b is from 2:1 to 30:1
  v:b is from 1.5:to 8:1
and 2) is made by preforming a bismuth molybdate containing composition having at least 0.67, usually at least 1.5, atoms of Mo per atom of Bi, before combining with any vanadium compound.

Catalysts set forth in the process of the present claims could be made within the broad teachings of U.S. Pat. Nos. 4,148,757 and 4,212,766, although no catalyst is disclosed which contains vanadium. In any event there is no appreciation in these references that such catalyst would be useful in the presently claimed process for the partial oxidation of propane.

The catalyst can be prepared by making aqueous slurries from various starting material, with a variety of oxidation states for any of the elements in each component. They can be prepared as partially dried powders, which can then be redispersed in an aqueous or non-aqueous liquid medium to form the final catalyst. They can be intimately mixed, as by ball-milling, before or during this redispersion. Each component can incorporate a support material, especially colloidal silica, titania or alumina, before or after combination with the other component. Once the two components are combined, they can be fabricated into any practical catalyst form. Spray drying to form fluidizable microspheres, coating as a powder or slurry on a macroporous inert support, and extrusion, or other molding process, are but a few examples of such fabrication. The composition is calcined before or after the forming step, with calcination after generally preferred. The calcination temperature can be any required to decompose the starting materials and form the oxides, generally 300°–1000° C. Temperatures near 400°–650° C. are usual.

The catalysts can be used in any known reactor for partial oxidation. The reactor can be a fluidized bed or a transport reactor. The process can be carried out at any useful pressure, with 1–40 ATH being usual and 2–10 ATM most usual. Process temperature is set by the activity and stability of the individual catalysts, with 300°-600° C. usual, although other temperatures and pressures are possible. The propane feed for the process need not be pure and for instance, can contain propylene.

Molecular oxygen sources for the feed include purified oxygen, air and oxygen enriched air depending on the economics of separation and the hydrocarbon conversion achieved. The ratio of propane to oxygen varies with the desired conversion and the selectivity of the catalyst, but generally is in the range of 5/1-1/1. Reaction can also be effected especially in the presence of diluents such as nitrogen or steam. Such diluents can be fed at 0-50 times the partial pressure of the propane, with 0.2-10 times being usual. The liquid products of the reaction can be separated from the unreacted feed hydrocarbons by condensation or scrubbing, usually by water or dilute acid.

The catalysts used in the specific examples of the present process were made as follows:

CATALYST EXAMPLE 1

Empirical Composition: $BiMo_{12}V_5Nb_{0.5}SbKO_x$.

Slurry A was prepared as follows: 10 g of ammonium vanadate were dissolved in 500 ml water, with heating. Separately, 1 g of oxalic acid and 5.1 g of antimony triacetate were added to 100 ml water, with stirring 1.7 g potassium hicarbonate were added to the antimony preparation yielding an opaque, white suspension. After 15 min. stirring, 8.5 g of niobium oxalate solution (9.5 wt % Nb) were added to this suspension, which was then heated to 70° C. with stirring. The resulting suspension was then added to the ammonium vanadate solution to obtain a slurry, which was stirred with heating 20 min. 30.9 g of ammonium heplamolybate dissolved in 100 ml water were then added to this slurry. The resulting suspension is Slurry A.

Slurry B was prepared as follows: 2 g of glacial acetic acid and 6.5 g of bismuth triacetate were added to 50 ml of water. 4.46 of ammonium heptamolybdate dissolved in 50 ml of water were added, resulting in a slurry. This Slurry B was combined with Slurry A to obtain a suspension. Most of the water was thereafter evaporated by heating while stirring. The rest of the water was removed in a 110° C. oven overnight.

The material obtained after drying was homogenized by grinding to less than 60 Mesh to obtain 55 g of powder. Poly(vinylalcohol) solution (8 g, 2% wt PVA, 1 wt % acetic acid) was added as a binder and the resulting paste dried again at 110° C. It was then calcined at 290° C. and 425° C., 3 hr each. The resulting solid was ground and screened, and had surface area of 5.2 sq.m/g.

CATALYST EXAMPLE 2

Empirical Composition: $Bi_2Mo_{12}V_5Nb_{0.5}SbKO_x$.

Slurry A was made similarly to that for Example 1, except 26.5 g ammonium heptamolybdate was used. To prepare Slurry B, all the quantities were twice those used for Example 1. The total ammonium heptamolybdate used to make the two slurries was still 35.3 g. After the two slurries were combined, the resulting slurry was heated with stirring until a paste formed, which was then dried at 110° C. overnight. The resulting solid was calcined at 290 and 425° C., 3 hr each. Surface area was 5.0 sq.m/g.

CATALYST EXAMPLE 3

Empirical Composition: $BiMo_{12}V_5Nb_{0.5}SbKO_x$ with silica support.

Slurry A was made the same as for Example 1. When preparing Slurry B, silica sol (12 g, 40% $SiO_2$) was added to the molybdate solution before adding the bismuth acetate. Once the bismuth acetate was added, Slurry B was stirred 15 min before adding to Slurry A. The resulting suspension was stirred 2 hr, then heated to evaporate it to near dryness while stirring. The paste was dried at 110° C. overnight. After breaking into granules, the resulting solid was calcined at 290 and 425° C., for 3 hr each. Surface area was 10.7 Sq. m/g.

COMPARATIVE CATALYST A

Empirical Formula: $BiMo_{12}V_5Nb_{0.5}SbKO_x$.

Dissolved 10 g ammonium vanadate in 500 ml water, with heating. Separately, added 5.1 g antimony (III) triacetate 6.5 g bismuth triacetate and 1.7 g potassium nitrate to 100 ml water, with stirring. Added 0.8 g niobium oxalate, as $Nb(HC_2O_4)_5$, to the Bi-Sb-K suspension and heated to 70° C. with stirring. Combined the Nb-Bi-Sb-K suspension with the vanadate solution, to obtain a slurry with low viscosity. Next, dissolved 35.4 g ammonium heptamolybdate in 100 ml water and added to the V-Nb-Bi-Sb-K containing slurry. After stirring and heating, the paste formed after water was evaporated, was then dried in a 110° C. oven overnight. The resulting granules were calcined at 290° C. and 425° C., 3 hr each. The resulting solid was ground and screened, and had surface area of 8.2 sq.m/g.

Slurry A was made similarly to that for Example 1, except 26.5 g

COMPARATIVE EXAMPLE B

Empirical Composition: $Bi_3Mo_{12}V_5Mb_{0.15}SbKO_x$.

Dissolved 9.9 g ammonium vanadate in 500 ml water, with heating. Separately, added 0.8 g niobium ethoxide to 2 g ethanol, then added this solution dropwise to 100 ml water. A milky white suspension forms. This suspension was stirred while 5.1 g antimony (III) triacetate and 1.7 g potassium nitrate were added. Combined the Nb-Sb-K suspension with the vanadate solution, to obtain a slurry with low viscosity. Next, 24.7 g bismuth nitrate pentahydrate were dissolved in 110 ml 10% nitric acid. When this Bi solution was added to the V-Nb-Sb-K suspension increased and it took on a gold color. Finally, 35.3 g ammonium heptamolybdate was stirred in 100 ml of water at 70° C. and added to the V-Nb-Bi-Sb-K containing slurry. After stirring and heating, the gold suspension darkened to brick red. The paste formed after water was evaporated while stirring was then dried to a 110° C. oven overnight. The resulting granules were calcined at 290° C. and 425° C., 3 hr each. The resulting solid was ground and screened, and had surface area of 5.2 sq.m/g.

EXAMPLE 4

Empirical Composition: $BiMo_{12}V_5Nb_{0.15}Cu_{0.5}W_{0.5}SbKO_x$

This catalyst was prepared in the same manner at Example 1, except that in preparing Slurry A: (1) less of the niobium oxalate was used, enough to satisfy $Nb_{0.15}$ in the foregoing empirical formula, (2) sufficient $Cu_2O$ and $(NH_4)H_2W_{12}O_{40}\cdot H_2O$ were added to the Sb-K-Nb suspension to satisfy $Cu_{0.5}$ and $W_{0.5}$ in the foregoing empirical formula, the $Cu_2O$ being first added.

The final catalyst had a surface area of 4.7 sq. m/g.

EXAMPLE 5

Empirical Composition: $Bi_{1.5}Mo_{24}V_{10}Fe_{0.5}NbSb_2K_2O_x$.

This catalyst was prepared as described for Example 1 except for the following:

(1) In making Slurry A no oxalic acid was added.

(2) In making Slurry B ferric acetate was added with the bismuth triacetate, in an amount sufficient to satisfy the empirical composition noted above.

In the oxidation examples that are summarized in Table 1, both as to conditions and results, the catalyst was in a fixed bed in a ⅜ inch tubular 316 stainless steel reactor equipped with a preheat zone enclosed in a suitcase furnace. The feed to the reactor was fed downflow for at least one hour before collection of product for 30–60 minutes for analysis.

TABLE 1

| Oxidation Example No. | Catalyst Example No. | CT[3] Secs | Press. psig | Temp. °C. | Feed Mol Ratios $C_3/O_2/H_2O$[4] | Percent HC Conversion | Yield/Selectivity (Percent) | | | | |
|---|---|---|---|---|---|---|---|---|---|---|---|
| | | | | | | | Acrolein | Acrylic Acid | $C_3=$[1] | HOAc | AA + Acrol +[2] $C_3=$ + HOAc |
| I | 1 | 3 | 20 | 400 | 5/2/12 | 19.0 | 0.2/1 | 5.4/29 | 4.0/21 | 2.4/13 | 12/63 |
| II | A | 2.8 | 20 | 400 | 5/2/13 | 11.0 | 0.1/1 | 1.0/9 | 1.7/15 | 2.6/24 | 5.4/49 |
| III | B | 3.0 | 20 | 400 | 5/2/13 | 8.7 | 0.1/1 | 0.4/5 | 0.5/5 | 2.1/24 | 3.1/35 |
| IV | 4 | 2.1 | 20 | 375 | 5/2/13 | 10.0 | 0.07/0.7 | 2.3/23 | 2.6/26 | 1.2/12 | 6.2/62 |
| V | 2 | 3.2 | 20 | 425 | 5/2/11.1 | 14.6 | 0.1/1 | 4.0/27 | 4.4/30 | 1.0/7 | 9.5/65 |
| VI | 3 | 2.0 | 20 | 425 | 5/2/13 | 18.0 | 0.2/1 | 4.8/27 | 4.4/25 | 1.4/8 | 10.8/61 |
| VII | 3 | 2.0 | 20 | 400 | 5/2/13 | 18.0 | 0.2/1 | 4.9/28 | 3.6/20 | 2.8/16 | 11.5/65 |
| VIII | 5 | 2.0 | 20 | 375 | 5/2/14.6 | 15.0 | 0.2/1 | 3.6/24 | 2.8/19 | 3.1/21 | 9.7/65 |

[1]Propylene
[2]Acrylic acid + acrolein + propylene + HOAc
[3]Contact time
[4]$C_3$ is propane As will be evident to those skilled in the art, various modifications of this invention can be made or followed in the light of the foregoing disclosure and discussion without departing from the spirit and scope of the disclosure or from the scope of the claims.

We claim:

1. A process for the partial oxidation of propane to yield acrylic acid, propylene, acrolein and acetic acid by contacting propane in admixture with a molecular oxygen-containing gas in a reaction zone with an oxidic solid catalyst that 1) contains the components and proportions represented by the empirical formula $Bi_bMo_cV_vA_aD_dE_eO_x$ wherein
   A is one or more of K, Na, Li, Cs and Tl,
   D is one or more of Fe, Ni, Co, Zn, Ce and La,
   E is one or more of W, Nb, Sb, Sn, P, Cu, Pb, B, Mg, Ca and Sr,
   a, d and e are each zero–10
   b is 0.1–10
   c is 0.1–20
   v is 0.1–10
   c:b is from 2:1 to 30:1
   v:b is from 1.5:1 to 8:1
   and 2) is made by preforming a bismuth molybdate containing composition having at least 0.67 atoms of Mo per atom of Bi, before combining with any vanadium compound.

2. A process of claim 1 wherein the catalyst is made by preforming a bismuth molybdate composition having at least 1.5 of Mo per atom of Bi, before combining with any vanadium compound.

* * * * *

UNITED STATES PATENT AND TRADEMARK OFFICE
CERTIFICATE OF CORRECTION

PATENT NO. : 5,198,580
DATED : 03-30-1993
INVENTOR(S) : Joseph P. Bartek, et al.

It is certified that error appears in the above-indentified patent and that said Letters Patent is hereby corrected as shown below:

On the title page, item (75): Inventors, James R. Brazdil, should read --James F. Brazdil--.

Signed and Sealed this

Fifth Day of April, 1994

Attest:

BRUCE LEHMAN

*Attesting Officer*   *Commissioner of Patents and Trademarks*